(12) United States Patent
André et al.

(10) Patent No.: US 10,920,421 B2
(45) Date of Patent: Feb. 16, 2021

(54) NON-FLAMMABLE LAMINATE

(71) Applicant: DI DEKODUR INTERNATIONAL GMBH & CO KG IG, Hirschhorn (DE)

(72) Inventors: Volkmar André, Hirschhorn (DE); Holger Held, Erbach im Odenwald (DE)

(73) Assignee: DI DEKODURINTERNATIONAL GMBH & CO. KG, Hirschhorn (DE)

( * ) Notice: Subject to any disclaimer, the term of this patent is extended or adjusted under 35 U.S.C. 154(b) by 73 days.

(21) Appl. No.: 15/528,135

(22) PCT Filed: Nov. 19, 2015

(86) PCT No.: PCT/EP2015/077117
§ 371 (c)(1),
(2) Date: May 19, 2017

(87) PCT Pub. No.: WO2016/079245
PCT Pub. Date: May 26, 2016

(65) Prior Publication Data
US 2017/0328063 A1 Nov. 16, 2017

(30) Foreign Application Priority Data

Nov. 20, 2014 (DE) .......................... 10 2014 116 984

(51) Int. Cl.
*E04C 2/24* (2006.01)
*B32B 5/02* (2006.01)
(Continued)

(52) U.S. Cl.
CPC .............. *E04C 2/246* (2013.01); *B32B 5/022* (2013.01); *B32B 5/22* (2013.01); *B32B 5/24* (2013.01);
(Continued)

(58) Field of Classification Search
CPC .. E04C 2/246; B32B 5/22; B32B 5/24; B32B 2607/00; B32B 2419/00; B32B 2307/3065
See application file for complete search history.

(56) References Cited

U.S. PATENT DOCUMENTS 3,736,220 A    5/1973  Bipin Manubahi Shah
5,085,921 A *  2/1992  Jayarajan ................ B32B 27/06
                                                    156/219
(Continued)

FOREIGN PATENT DOCUMENTS

DE           49344 A  *  8/1966
DE         2907707       9/1980
(Continued)

OTHER PUBLICATIONS

English-language machine translation of DE2907707 (1980), performed on Espacenet website, Nov. 29, 2018, six pages.*
(Continued)

*Primary Examiner* — Nicholas E Hill
(74) *Attorney, Agent, or Firm* — Grossman. Tucker, Perreault & Pfleger, PLLC

(57) ABSTRACT

The invention relates to a laminate, in particular for manufacturing a construction panel, consisting of a combination of at least one carrier material layer made of a non-flammable non-woven impregnated with a resin and at least one decorative material layer made of a decorative paper that is impregnated with a melamine formaldehyde resin and is optionally dyed and/or printed. The invention further relates to a method for manufacturing a disclosed laminate and especially a construction panel.

13 Claims, 3 Drawing Sheets

(51) Int. Cl.
*B32B 5/24* (2006.01)
*B32B 19/04* (2006.01)
*B32B 19/06* (2006.01)
*B32B 29/02* (2006.01)
*B32B 19/00* (2006.01)
*B32B 5/22* (2006.01)
*B32B 29/00* (2006.01)
*B32B 17/02* (2006.01)

(52) U.S. Cl.
CPC .............. *B32B 17/02* (2013.01); *B32B 19/00* (2013.01); *B32B 19/046* (2013.01); *B32B 19/06* (2013.01); *B32B 29/00* (2013.01); *B32B 29/02* (2013.01); *B32B 2250/00* (2013.01); *B32B 2250/02* (2013.01); *B32B 2250/03* (2013.01); *B32B 2250/20* (2013.01); *B32B 2250/26* (2013.01); *B32B 2250/40* (2013.01); *B32B 2255/00* (2013.01); *B32B 2255/02* (2013.01); *B32B 2255/12* (2013.01); *B32B 2260/00* (2013.01); *B32B 2260/021* (2013.01); *B32B 2260/023* (2013.01); *B32B 2260/028* (2013.01); *B32B 2260/046* (2013.01); *B32B 2307/3065* (2013.01); *B32B 2307/724* (2013.01); *B32B 2419/00* (2013.01); *B32B 2607/00* (2013.01)

(56) References Cited

U.S. PATENT DOCUMENTS

| | | | | |
|---|---|---|---|---|
| 6,333,280 | B1* | 12/2001 | Hashimoto | B32B 5/28 442/70 |
| 9,650,783 | B2 | 5/2017 | Ullrich et al. | |
| 2002/0046527 | A1* | 4/2002 | Nelson | E04F 15/04 52/582.1 |
| 2006/0234026 | A1* | 10/2006 | Huusken | B32B 5/022 428/292.1 |
| 2007/0012412 | A1* | 1/2007 | Goodrow | B32B 27/10 162/123 |
| 2008/0090032 | A1* | 4/2008 | Perrin | B44C 5/04 428/32.21 |
| 2010/0272976 | A1* | 10/2010 | Ashton | B32B 27/08 428/215 |
| 2013/0216796 | A1* | 8/2013 | Correa | B32B 13/04 428/206 |
| 2013/0323497 | A1* | 12/2013 | Ullrich | B32B 5/26 428/316.6 |

FOREIGN PATENT DOCUMENTS

| | | |
|---|---|---|
| DE | 102007037137 | 2/2009 |
| EP | 0899092 | 3/1999 |
| EP | 2156950 | 2/2010 |
| EP | 2431173 | 3/2012 |
| EP | 2732943 | 5/2014 |
| WO | 2006/111458 | 10/2006 |

OTHER PUBLICATIONS

English-language abstract of DD49344A from Derwent. (Year: 1968).*
Wikipedia definition of "Vliesstoff" and English translation.
Wikipedia definition of "Quarzfaser" and English translation.
English translation of International Search Report from corresponding PCT Appln. No. PCT/EP2015/077117 dated Feb. 9, 2016.
English translation of Written Opinion from corresponding PCT Appln. No. PCT/EP2015/077117 dated May 26, 2016.

* cited by examiner

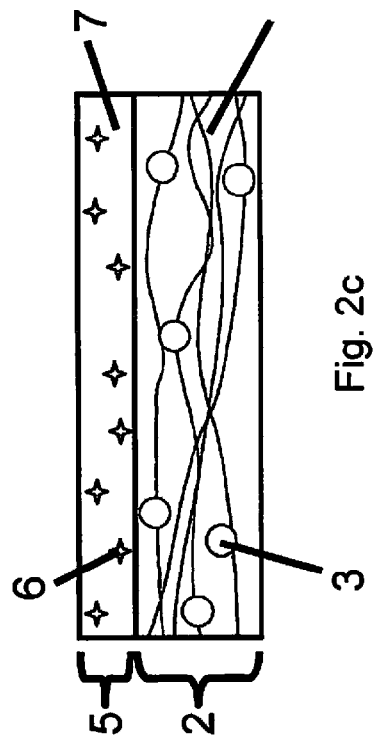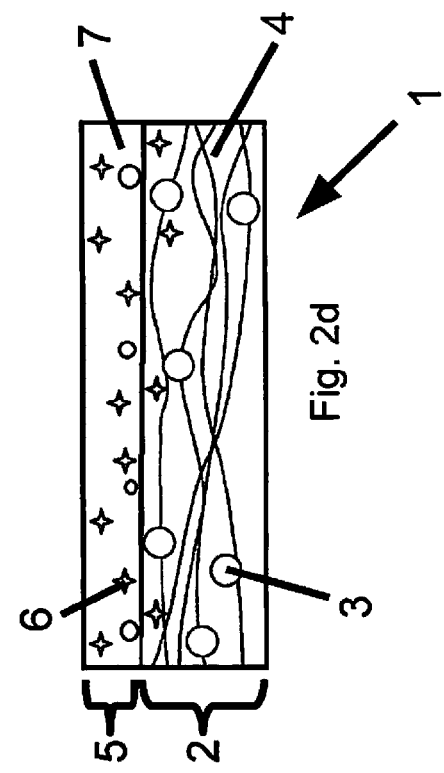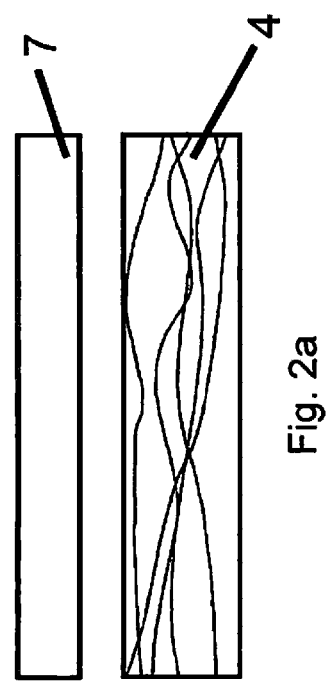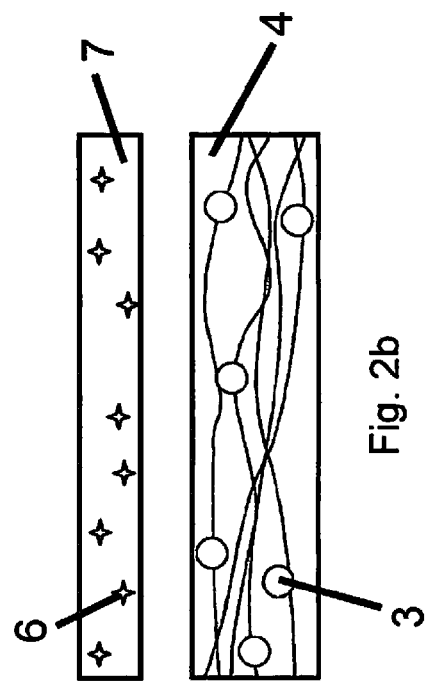

NON-FLAMMABLE LAMINATE

FIELD

The invention relates to a laminate, in particular for manufacturing a construction panel as well as to a method for manufacturing a laminate according to the invention and in particular a construction panel.

BACKGROUND

It is known from the state of the art to use panels made of laminate both indoor and outdoor. Depending on the application field, such panels have to meet different requirements. Laminate panels having a decoratively designed surface will be for example used in the furniture industry, in the household sector, at public places and in many other application fields.

For manufacturing decorative laminate panels, a layer structure is formed, in which at first one or more layers of carriers impregnated with synthetic resin will be placed on a stable plate which will later be introduced into a panel press for being pressed with a pressure of more than 5 MPa. Herein, also inorganic carriers, such as non-woven fabrics, for example made of glass or mineral fibers, can be used.

The resin used for impregnating the base body usually is a resin curable by thermosetting, such as for example a phenol-formaldehyde resin, wherein from the technical point of view also other pre-condensates which are curable by thermosetting, such as melamine or urea resins as well as resins on the base of natural substances are however suitable.

One or more layers of paper can be placed on the base body impregnated with a resin, which paper layers are also impregnated with a resin, such as for example melamine resin. These layers of paper form the top layer of a laminate panel and are also referred to as decorative layer.

Usually pure cellulose paper is used as carrier for the decorative layer, which cellulose paper has its own effect thanks to a pigmentation or can additionally be printed and/or dyed and will be pressed together with the base body impregnated with a resin in a heated press at high temperature and surface pressure under the effect of a corresponding pressure and heat.

A synthetic resin which is as colorless as possible is used as binding agent for the decorative layer, preferably a melamine formaldehyde resin due to its long durability. Furthermore, also urea resins or melamine-urea mixed resins can be used for impregnating the decorative layer. Principally, other layers can be placed on the decorative layer, which other layers serve for example to improve the wear resistance of the surface, to obtain optical effects or for other purposes, such as for example the fire protection.

In order to meet the requirements of fire protection, a panel is known from DE 10 2007 037 137 A1 which consists of a glass fiber panel and a panel made of a hardly inflammable or non-flammable material which is placed on this one. It is in particular a disadvantage of the panel known from the state of the art that the composite comprises a high total thickness which is 5 mm or more. Especially if such a panel is used as a decorative panel, it is required to obtain a small total thickness in order to be able to meet the esthetic requirements. However, the partly legally prescribed requirements with respect to the fire protection have still to be observed.

In this context it is the object of the present invention to provide an improved laminate which in particular comprises a small total thickness and furthermore has got sufficient fire protection properties in particular with respect to the fire protection class A1 according to DIN 4102-1 or EN 13501.

SUMMARY

For the technical solution the present invention proposes a laminate, in particular for manufacturing a construction panel, wherein the laminate consists of a combination of at least one carrier material layer made of a non-flammable non-woven fabric impregnated with a synthetic resin and at least one decorative material layer made of a decorative paper that is impregnated with a melamine formaldehyde resin and is optionally dyed and/or printed, wherein the laminate comprises a total thickness of less than 2.2 mm, preferably comprised between 0.3 mm and beneath 2.2 mm, most preferably between 0.5 mm and 1.3 mm, and a calorific value of less than 2 MJ/kg according to ISO 1716.

The invention makes in particular use of the knowledge that within the scope of manufacturing or preparing a laminate according to the invention it is possible to produce a non-flammable composite material on the base of the combination of a non-flammable non-woven fabric that is impregnated with a synthetic resin with a decorative material layer made of a decorative paper that is impregnated with a melamine formaldehyde resin, which composite material furthermore comprises a small total thickness as well as a low total weight. This is in particular obtained by pressing the layers together according to the method according to the invention.

In an advantageous embodiment of the invention it is provided that a glass fiber non-woven fabric will be used as carrier material layer of the laminate. Thanks to the use of a glass fiber non-woven fabric the carrier material layer will in particular show improved properties with respect to the fire protection, since an inflammation will not be easily possible.

In another advantageous embodiment of the invention it is provided that the carrier material layer of the laminate is made of quartz glass fibers, since these ones comprise a high chemical resistance, a high softening temperature as well as a higher disruptive strength. Thereby, the carrier material layer of the laminate does not only become more resistant against a fire, but also more stable.

Another advantageous embodiment of the invention furthermore provides that the carrier material layer consists of a random orientation fleece. In a random orientation fleece the staple fibers or the filaments can be directed into any random direction, such that a higher stability results from this equal distribution into all directions of the non-woven fabric. According to another advantageous embodiment of the invention it is provided that the non-woven fabric is a woven fleece material which means that the fleece material has a woven structure, a knitted fleece material or any other non-flammable fleece material or the like. Thanks to such a design, the laminate as an entire composite material will be more resistant with respect to fire protection.

In another advantageous embodiment of the invention a crosslinker is used as additive in the synthetic resin that is used for impregnating the carrier material layer. The use of a crosslinker in the used synthetic resin makes it possible to obtain both an increased hardness and an increased tenacity and flexibility of the laminate according to the invention.

In another advantageous embodiment of the laminate according to the invention it is provided that a metal hydroxide, metal carbonate, titanium oxide, calcinated loess, barium sulfate, magnesium sulfate, aluminum sulfate, zinc oxide, kaolin, chlorite, diatomite, feldspar, mica, nepheline syenite, pyrophyllite, silicon, talcum, wollastonite, montmorillonite, hectorite, saponite, calcium carbonate, magnesium carbonate, aluminum oxide, iron oxide, magnesium hydroxide and/or micro-spheres made of glass will be used as filling material in the synthetic resin which is used for impregnating the carrier material layer. Thanks to the use of one or more of the mentioned filling materials, the properties of the synthetic resin, which is used for impregnating the carrier material layer, with respect to its use for fire protection will be further improved, in particular such that the calorific value of the laminate will be reduced and that this will have a sustainable effect on the general fire behavior.

According to a preferred embodiment of the laminate according to the invention, only one carrier material layer is used, since in this manner both the total thickness and the weight of the laminate can be kept small.

In another advantageous embodiment of the laminate according to the invention it is provided that the decorative paper to be impregnated comprises a specific surface weight comprised between 22 g/m² and 220 g/m². The use of an especially light decorative paper enables to use a laminate according to the invention also in fields where only low weights may be used, such as for example for the coating of construction panels. If however a high weight of the laminate is required, for example for a higher stability, a decorative paper having a high specific surface weight of the several decorative paper layers placed one on top of the other will be used.

Advantageously, the decorative paper to be impregnated of the laminate according to the invention comprises a porosity according to Gurley of less than 20 s/100 ml according to ISO 5636/5, since hereby the absorption of the synthetic resin used for the impregnation can be substantially improved.

In another advantageous embodiment of the laminate, the decorative paper to be impregnated comprises a smoothness of Bekk of more than 70 s/Bekk according to ISO 5627, since hereby a better optical appearance is realized, on the one hand, and furthermore an improved preparation of the surface for an optional later coating with another additive can be obtained, on the other hand.

In another especially advantageous embodiment of the laminate according to the invention, the decorative paper to be impregnated comprises a penetration of less than 5 s according to ISO 5633 with respect to the melamine formaldehyde resin used for the impregnation. Thereby, it is in particular enabled to absorb high quantities of the melamine formaldehyde resin, which leads to improved fire protection properties.

In an advantageous embodiment of the laminate according to the invention it is furthermore provided that the decorative paper to be impregnated will be preferably produced from short fibers and/or long fibers in the sheet forming process. The use of short fibers can make sense, if the laminate to be manufactured has to meet increased requirements with respect to the stability, whereas long fibers can be used, if it is desired to embed a predetermined breaking point in the laminate.

In another advantageous embodiment of the invention it is provided that the decorative paper to be impregnated comprises an ash content of at least 20% by weight. The use of a high ash content in the decorative paper leads to a reduction of the proportion of flammable components in the decorative paper and thus the properties with respect to the calorific value will be weakened, whereby the entire fire resistance of the laminate can be further increased.

In an advantageous embodiment of the laminate according to the invention, a dye consisting of inorganic substances will be used for dyeing and/or printing the decorative paper to be impregnated. This is in particular advantageous for an improved fire behavior, since the use of a dye consisting of inorganic substances further increases the resistance of the laminate against fire.

Advantageously, titanium oxide, talcum or the like will be used as filling material in the melamine formaldehyde resin used for impregnating the decorative paper of the laminate according to the invention. Such substances are thermally stable and comprise a particularly high melting point, such that this property can be used for further improving the fire behavior.

In an advantageous embodiment of the laminate according to the invention, the surface of the decorative material layer which is facing away from the impregnated carrier material layer is provided with a flame retardant. The use of a flame retardant offers an additional protection of the fire resistant decorative material layer, in particular because it becomes more difficult for flames which attack the laminate in case of fire to get into contact with the decorative material layer at all.

The above mentioned disadvantages of the state of the art will be furthermore removed by means of a method for manufacturing a laminate which meets the requirements of the building material class A1 according to DIN 4102-1 or EN 13501, wherein at least one carrier material layer made of a non-flammable non-woven fabric which is impregnated with a synthetic resin will be pressed together with a decorative material layer made of a decorative paper that is impregnated with a melamine formaldehyde resin and optionally dyed and/or printed into a composite, such that the laminate resulting from the pressing comprises a total thickness of less than 2.2 mm, preferably comprised between 0.3 mm and 2.2 mm, most preferably between 0.5 mm and 1.3 mm and a calorific value of less than 2 MJ/kg.

A preferred embodiment of the method according to the invention provides that the carrier material layer will be grinded before being impregnated with the synthetic resin. In this manner, a better absorption of the synthetic resin used for the impregnation is obtained.

According to another advantageous embodiment of the method according to the invention a flame retardant will be applied onto the surface of the decorative material layer facing away from the carrier material layer after having pressed the impregnated carrier material layer together with the impregnated decorative material layer. Hereby an improved fire behavior can be obtained, since in case of fire the flame retardant will prevent the flames form reaching the decorative material layer at all.

Another advantageous embodiment of the method according to the invention provides that during the pressing operation the synthetic resin used for impregnating the carrier material layer and the melamine formaldehyde resin used for impregnating the decorative material layer will mix with each other. Thanks to the mixing of both resins, which results from the fact that these resins are also present in the border area of the two layers, the laminate is further improved with respect to its fire behavior.

Another advantageous embodiment of the method according to the invention provides that the pressing operation will be carried out at an increased temperature and high surface pressure by means of a one-level or multi-level press or a continuous double belt press with or without back cooling. The use of a multi-level press can increase the manufacturing efficiency, wherein the use of a one-level press also enables the production of a small number of pieces. Thanks to the presence of a back cooling, the properties of the laminate according to the invention can be in particular further improved by means of the method according to the invention.

BRIEF DESCRIPTION OF THE DRAWINGS

Other details, features and advantages of the invention will explained in more detail in the following by means of the exemplary embodiments represented in the figures of the drawings.

FIGS. 2a to 2d are schematic cut views which show an exemplary embodiment of a method according to the invention for manufacturing a laminate.

DETAILED DESCRIPTION

Figure 1:
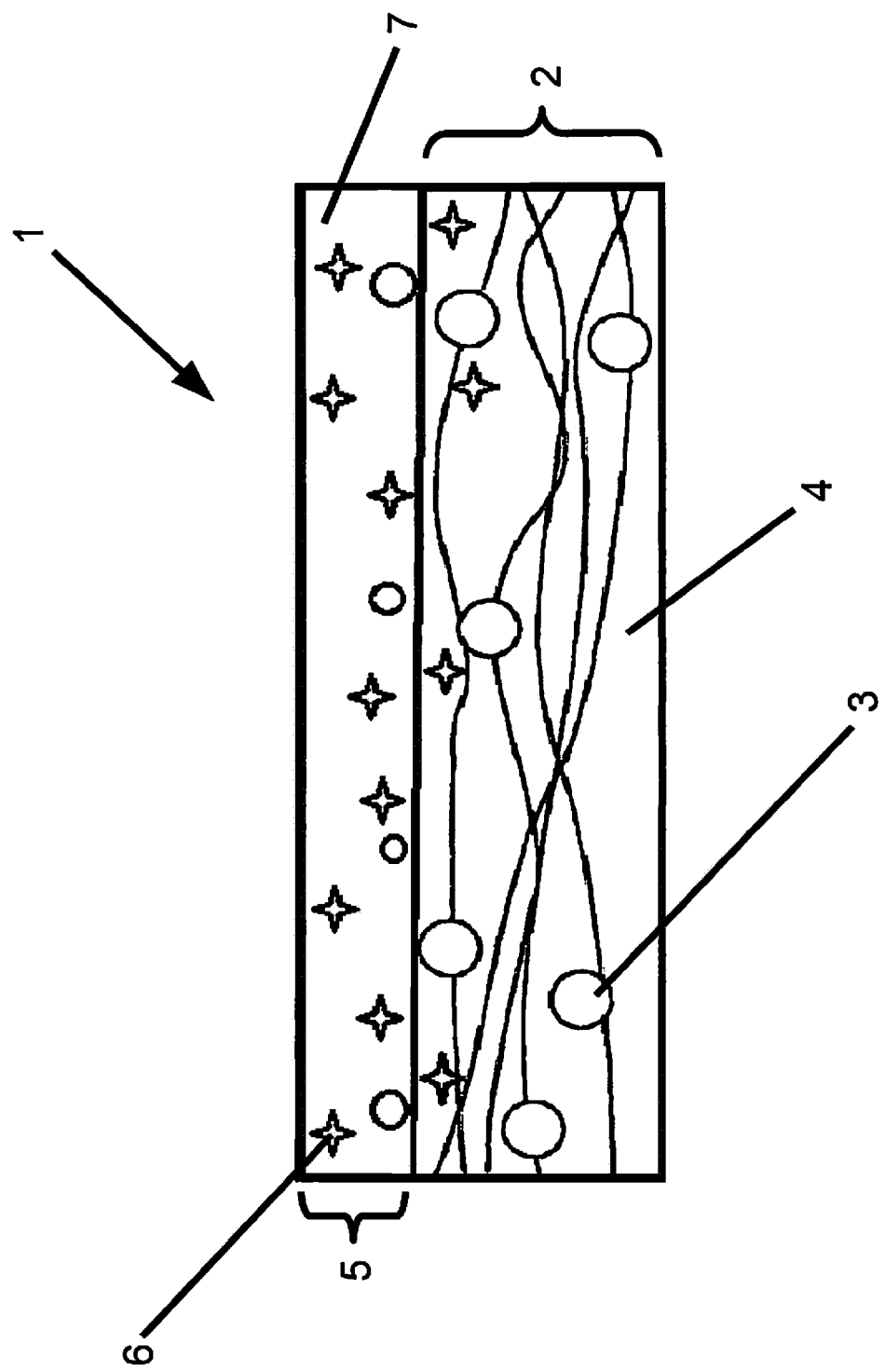
FIG. 1 is a schematic cut view which shows an exemplary embodiment of a laminate according to the invention.

FIG. 1 shows a schematic cut view of a laminate 1. The laminate 1 consists of a composite formed of a carrier material layer 2 and a decorative material layer 5. Herein, the carrier material layer 2 consists of non-flammable non-woven fabric 4 which is impregnated with a synthetic resin 3. The decorative material layer 5 however consists of a decorative paper 7 that is impregnated with melamine formaldehyde resin 6. Furthermore, it is visible in FIG. 1 that in a laminate which has been manufactured by means of the method according to the invention the synthetic resin 3 used for impregnating the carrier material layer 2 and the melamine formaldehyde resin 6 used for impregnating the decorative material layer 5 have mixed with each other, which leads to a further improvement of the laminate 1 with respect to its fire behavior.

FIG. 2a (first process step) is a schematic cut view which shows a non-flammable non-woven fabric 4 for a carrier material layer as well as an optionally dyed and/or printed decorative paper 7 for a decorative material layer. Neither the non-woven fabric 4 nor the optionally dyed and/or printed decorative paper 7 are impregnated with a synthetic resin and connected with each other in this process step.

FIG. 2b (second process step) is a schematic cut view which shows a non-flammable non-woven fabric 4 that is now impregnated with a synthetic resin 3 as well as an optionally dyed and/or printed decorative paper 7 that has been impregnated with a melamine formaldehyde resin 6. The impregnation of the two individual components which are required for a laminate that consists of a composite, can take place sequentially or in parallel. Furthermore, it is imaginable that an already preconfigured layer of a non-woven fabric 4 that is impregnated with a synthetic resin 3 and/or of an optionally dyed and/or printed decorative paper 7 that is impregnated with a melamine formaldehyde resin 6 will be used.

FIG. 2c (third process step) is a schematic cut view which shows the pressing of a non-flammable non-woven fabric 4 which is impregnated with a synthetic resin 3 with an optionally dyed and/or printed decorative paper 7 that is impregnated with a melamine formaldehyde resin 6 into a composite. Herein, the pressing operation will be carried out at an increased temperature and high surface pressure by means of a one-level or multi-level press or a continuous double belt press with or without back cooling. The laminate known from FIG. 1 can be manufactured by means of such a pressing operation.

FIG. 2d (fourth process step) is a schematic cut view which shows a laminate 1 according to the invention in the form of a composite which results from the pressing of the carrier material layer 2 made of a non-flammable non-woven fabric 4 which is impregnated with a synthetic resin 3 with a decorative material layer 5 made of an optionally dyed and/or printed decorative paper 7 that is impregnated with a melamine formaldehyde resin 6. It is furthermore visible in FIG. 2d that during the pressing of both material layers, the synthetic resin 3 used for impregnating the carrier material layer 2 and the melamine formaldehyde resin 6 used for impregnating the decorative material layer 5 have mixed with each other, in particular in the border area of the two material layers. Thanks to such a mixing of the different resins the laminate is further improved with respect to its fire behavior.

Figure 3:
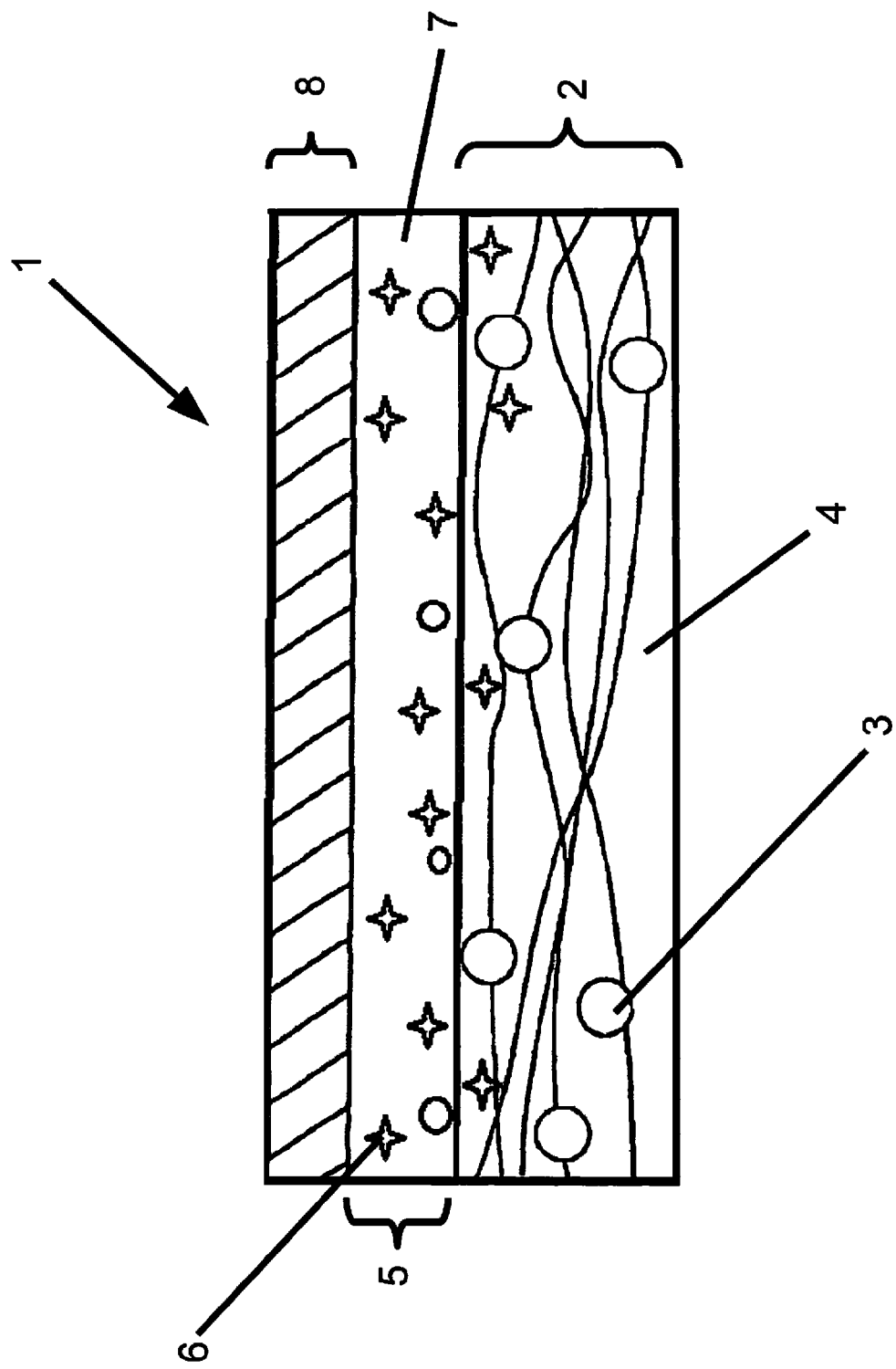
FIG. 3 is a schematic cut view which shows another exemplary embodiment of a laminate according to the invention.

FIG. 3 is a schematic cut view which shows a laminate according to the invention, in which the surface of the decorative material layer 5 which is facing away from the impregnated carrier material layer 2 is provided with a flame retardant. This serves in particular to further improve the laminate 1 according to the invention with respect to its fire behavior.

The exemplary embodiments represented in the figures of the drawing and the exemplary embodiments explained in connection with these ones only serve for explaining the invention and are not limiting for this one.

LIST OF REFERENCE NUMERALS 1 laminate
2 carrier material layer
3 synthetic resin
4 non-woven fabric
5 decorative material layer
6 melamine formaldehyde resin
7 decorative paper
8 flame retardant

What is claimed is:

1. A laminate for manufacturing a construction panel, comprising:
   at least one carrier material layer made of a non-flammable non-woven fabric impregnated with a first synthetic resin; and
   at least one decorative material layer made of a decorative paper that is impregnated with a second synthetic resin, the second synthetic resin being different from the first synthetic resin, wherein the second synthetic resin comprises melamine formaldehyde resin, wherein the decorative paper to be impregnated comprises a specific surface weight comprised between 22 g/m$^2$ and 220 g/m$^2$ and an ash content of at least 20% by weight, wherein the laminate comprises a total thickness of less than 2.2 mm and a calorific value of less than 2 MJ/kg according to ISO 1716, and wherein a surface of the decorative material layer which is facing away from the impregnated carrier material layer is provided with a flame retardant.

2. The laminate according to claim 1, wherein the non-woven fabric is a glass fiber non-woven fabric.

3. The laminate according to claim 1, wherein the non-woven fabric consists of quartz glass fibers.

4. The laminate according to claim 1, wherein the non-woven fabric is a random orientation fleece.

5. The laminate according to claim 1, wherein the non-woven fabric is a knitted fleece material or any other non-flammable fleece material.

6. The laminate according to claim 1, wherein the synthetic resin includes a crosslinker in the form of an additive for impregnating the non-woven fabric.

7. The laminate according to claim 1, wherein a metal hydroxide, metal carbonate, titanium oxide, calcinated loess, barium sulfate, magnesium sulfate, aluminum sulfate, zinc oxide, kaolin, chlorite, diatomite, feldspar, mica, nepheline syenite, pyrophyllite, silicon, talcum, wollastonite, montmorillonite, hectorite, saponite, calcium carbonate, magnesium carbonate, aluminum oxide, iron oxide, magnesium hydroxide and/or micro-spheres made of glass is present in the synthetic resin as a filling material for impregnating the non-woven fabric.

8. The laminate according to claim 1, wherein the decorative paper to be impregnated comprises a porosity according to Gurley of less than 20 s/100 ml according to ISO 5636/5.

9. The laminate according to claim 1, wherein the decorative paper to be impregnated comprises a smoothness of Bekk of more than 70 s/Bekk according to ISO 5627.

10. The laminate according to claim 1, wherein the decorative paper to be impregnated comprises a penetration of less than 5 s according to ISO 5633 with respect to the melamine formaldehyde resin used for the impregnation.

11. The laminate according to claim 1, wherein the decorative paper to be impregnated is produced from short fibers and/or long fibers.

12. The laminate according to claim 1, wherein the decorative paper includes a dye consisting of inorganic substances.

13. The laminate according to claim 1, wherein titanium oxide or talcum serve as a filling material in the melamine formaldehyde resin used for impregnating the decorative paper.

* * * * *